US005994141A

United States Patent [19]
Xu et al.

[11] Patent Number: 5,994,141
[45] Date of Patent: Nov. 30, 1999

[54] METHOD OF DETECTING GYNECOLOGICAL CARCINOMAS

[75] Inventors: Yan Xu, Mayfield Heights; Graham Casey, Moreland Hills, both of Ohio; Douglas C. Gaudette; Bruce J. Holub, both of Guelph, Canada; Gordon B. Mills, Houston, Tex.

[73] Assignee: The Cleveland Clinic Foundation, Cleveland, Ohio

[21] Appl. No.: 09/139,841

[22] Filed: Aug. 25, 1998

Related U.S. Application Data

[63] Continuation of application No. 08/655,551, May 30, 1996, Pat. No. 5,824,555.

[51] Int. Cl.⁶ .................................................. G01N 33/50
[52] U.S. Cl. .............................. 436/64; 436/63; 436/71; 436/161; 436/162; 436/103; 436/104; 436/105; 436/177
[58] Field of Search .................................. 436/63, 64, 71, 436/177, 103, 104, 105, 161, 162

[56] References Cited

U.S. PATENT DOCUMENTS

| | | |
|---|---|---|
| 4,999,344 | 3/1991 | Jett-Tilton, et al. . |
| 5,277,917 | 1/1994 | Xu et al. . |
| 5,326,690 | 7/1994 | Xu et al. . |
| 5,595,738 | 1/1997 | Pomato et al. . |
| 5,824,555 | 10/1998 | Xu et al. .................................. 436/64 |

FOREIGN PATENT DOCUMENTS

98/43093  10/1998  WIPO .

OTHER PUBLICATIONS

Xu et al. "Activation of Human Ovarian cancer cells: role of lipid factors in ascitic fluid" Ovarian Cancer 3—Chapter 13, p. 121–134, 1994.

Xu et al. "Lysophospholipids activate ovarian & breast cancer cells". Biochem. J. (1995), 309 933–940.

Xu et al. "Characterization of an Ovarian Cancer Activating Factor in Ascities from Ovarian Cancer Patients", Clinical Cancer Research vol. 1, 1223–1232, Oct. 1995.

Xu et al. Effect of Lysophospholipids on Signaling in the Human Jurical T Cell Line: Journal of Cellular Physiology 163:441–450, 1995.

Moolenaar, W. "Lysopholidic acid signalling". Current Opinion in Cell Biology; 7:203–210, 1995.

Moolenaar, W. "LPA: a novel lipid mediator with diverse biological actions". Trends in Cell Biology, 4, 213–218, 1994.

Eichholtz et al "The Bioactive phospholipid lysoplasphatidic acid is released from activated platelets". Biochem J. 291, 677–680, 1993.

Jalink et al. "Growth Factor–Like effects of lysophospholidic acid a novel lipid mediator". Biochimica of Biophysica Acta, 1198; 185–196, 1994.

"Lysophophatidylcholine Stimulates Activator Protein 1 and the c–Jun N–terminal Kinase Activity" by Fang, et al., *The Journal of Biological Chemistry*, vol. 272, No. 21, May 23, 1997, pp. 13683–13689.

"Peptide and Lipid Growth Factors Decrease cis –Diamminedichloroplatinum–induced Cell Death in Human Ovarian Cancer Cells" by Frankel, et al., *Clinical Cancer Research*, vol. 2, Aug. 2996, pp. 1307–1313.

"A Pueative New Growth Factor in Ascitic Fluid form Ovarian Cancer Patients: Identification, Characterization, and Mechanism of Action" by Mills, et al., *Cancer Research*, 42, Mar. 1, 1998, pp. 1066–1071.

"Ascitic Fluid from Ovarian Cancer Patients Contains Growth Factors Necessary for Intraperitoneal Growth of Human Ovarian Adenocarcinoma Cells" by Mills, et al., *J. Clin. Invest.*, vol. 86, Sep. 1990, pp. 851–855.

"Levels of soluble interleukin–2 receptor–α are elevated in serum and ascitic fluid from epithelial ovarian cancer patients" by Hurteau, et al.,*Am J. Obstet Gynecol*, vol. 170, No. 3, Mar. 1994, pp.918–928.

"Soluble Interleukin–2 Receptor Alpha is Elevated in Sera of Patients with Benign Ovarin Neoplasms and Epithelial Ovarian Cancer" by Hurteau, et al., *Cancer*, vol. 76, No. 9, Nov. 1, 1995, pp. 1615–1620.

"Induction of In Vitro Tumor Cell Invasion of Cellular Monoplayers by Lysophosphatidic Acid or Phospholipase D" by Imamura, *Biochemical and Biophysical Research Communications*, Vo. 193, No. 2, Jun. 15, 1993, pp. 497–503.

"Analysis of the Proliferative Response to Lysophosphatidic Acid in Primary Cultures of Mammary Epithelium: Differences between Normal and Tumor Cells" by Imagawa, et al., *Experimental Cell Research*, 216, pp. 178–186 (1995).

"Role of Growth Factors: Their Receptors and Signalling Pathways in the Diagnosis, Prognosis, Follow–up and Therapy of Ovarian Cancer" by Mills, et al. *Diagnostic Oncology*, 1992, 2:39–54.

"Lysophosphatidic acid: G–protein signalling and cellular responses" by Moolenaar, *Cell Regulation*, pp. 168–173.

Abstract #710, "Lysophosphatidic acid, a diagnostic biomarker for ovarian and other gynecological cancers" by Xu, et al., *Proceedings of the American Association for Cancer Research*, vol. 38, Mar. 1997, p. 106.

(List continued on next page.)

*Primary Examiner*—Jill Warden
*Assistant Examiner*—S. Carrillo
*Attorney, Agent, or Firm*—Calfee, Halter & Griswold LLP

[57] ABSTRACT

Methods for diagnosing and screening for ovarian carcinomas in a subject are provided The methods employ the steps of preparing a plasma sample from a blood specimen from the subject, and assaying for the presence of lysophosphatidic acid in the plasma sample. The presence of lysophosphatidic acid in the plasma sample is indicative of ovarian carcinoma in the subject. In a preferred embodiment the plasma sample is prepared under conditions which minimize the release of lysophosphatidic acid from platelets in the blood specimen into the plasma.

8 Claims, No Drawings

OTHER PUBLICATIONS

"Increased phophatidic acid and decreased lysophosphatidic acid in response to thrombin is associated with inhibition of platelet aggregation" by Gerrard, et al., *Biochem Cell Bio.*, vol. 71, 1993, pp. 432–439.

"LPA: a novel lipid mediator with diverse biological actions" by Moolenaar, *Trends in Cell Biology*, vol. 4, Jun. 1994, pp. 213–218.

"Lysophosphatidic Acid, a Multifunctional Phospholipid Messenger" by Moolenaar, *The Journal of Biological Chemistry*, vol. 270, No. 22, Jun. 2, 1995, pp. 12949–12952.

"Lysophosphatidic acid possesses dual action in cell proliferation" by Tigyi, et al. *Proc. Natl. Acad. Sci. USA*, vol. 91, Mar. 1994, pp. 1908–1912.

"Decanol lysophosphatidic acid induces platelet aggregation through an extracellular action" by Watson, et al., *Biochem. J.*, (1985) 232, pp. 61–66.

"Lysophosphatidic Acid as a Potential Biomarker for Ovarian and Other Gynecologic Cancers" by Xu, et al., *The Journal of the American Medical Association*, vol. 280, No. 6 Aug. 26, 1996, pp. 719–723.

"Phorbol 12–Myristate 13–Acetate Stimulates Lysophosphatidic Acid Secretions from Ovarian and Cervical Cancer Cells but not from Breast or Leukemia Cells" by Shen, et al., *Gynecologic Oncology*, 71, pp. 364–368 (1998).

"Elevated Levels and Altered Fatty Acid Composition of Plasma Lysophosphatidylcholine (LYSOPC) in Ovarian Cancer Patients" by Okita, et al., *Int. J. Cancer*, 71, 31–34 (1997).

"Malignant effusions contain lysophosphatidic acid (LPSA)-like activity" by Westermann, et al., *Annals of Oncology*, 9, pp. 437–442 (1998).

5,994,141

METHOD OF DETECTING GYNECOLOGICAL CARCINOMAS

This application is a continuation of application Ser. No. 08/655,551 filed on May 30, 1996, now U.S. Pat. No. 5,884,555.

BACKGROUND OF THE INVENTION

Gynecological carcinomas such as ovarian carcinoma, cervical carcinoma, endometrial carcinoma and peritoneal carcinoma are among the most frequent causes of cancer death among women in the United States and Europe. It is estimated that ovarian carcinoma alone will be responsible for 14,800 deaths in 1996 in the United States. This dismal outcome is due, at least in part, to an inability to detect the ovarian carcinoma at an early stage of tumor development. When ovarian carcinoma is diagnosed at an early stage, the cure rate approaches 90%. In contrast, the 5 year outlook for women with advanced disease remains poor with no more than a 15% survival rate. Thus, early diagnosis is one of the most effective means of improving the prognosis for ovarian carcinoma.

Transvaginal sonography is the most sensitive of the currently available techniques used for detecting ovarian tumors. However, transvaginal sonography is non-specific, i.e. it will detect benign as well as malignant tumors. Accordingly, detection of an ovarian tumor by transvaginal sonography must be followed by a second diagnostic procedure which is able to distinguish benign tumors from malignant tumors. Moreover, transvaginal sonography is very expensive and, therefore, not useful as a screening procedure for large numbers of patients.

Typically, benign ovarian tumors are distinguished from malignant ovarian tumors by surgical procedures such as biopsy of the mass or aspiration of the mass and cytological examination of the cells that are surgically removed from the patient. However, these techniques are highly invasive, expensive, and in the case of aspiration can lead to release of cancerous cells into the peritoneum.

The antigenic determinant CA 125, which is a high molecular weight mucin-like glycoprotein, is the current serum biomarker of choice for screening for ovarian carcinomas. However, CA 125 testing suffers from two main limitations. First of all, it is not very sensitive. For example, elevated serum CA 125 levels, i.e. levels above the cut-off point of 35 U/ml, are present in fewer than 50% of the patients with Stage I ovarian carcinoma. Taylor, K. J. W. and Schwartz, P. E., "Screening for Early Ovarian Cancer," Radiology, 192:1–10, 1994. In addition, CA 125 testing is not very specific. For example, approximately 25% of patients with benign gynecological diseases also have elevated serum levels of CA 125. Moreover, liver disease such as cirrhosis, even without ascites, elevates serum CA 125 levels above 35 U/ml. Taylor, K. J. W. and Schwartz, P. E., "Screening for Early Ovarian Cancer," Radiology, 192:1–10, 1994.

Accordingly, it would be desirable to have a new, simple, noninvasive or marginally invasive method for detecting gynecological carcinomas, particularly ovarian carcinomas, which is sufficiently sensitive to identify those subjects with early stage ovarian carcinoma, and sufficiently specific to distinguish between benign and malignant gynecological carcinomas.

SUMMARY OF THE INVENTION

The present invention provides a new, simple, marginally invasive method for detecting the presence of gynecological carcinomas in a patient. The method comprises detecting the presence of lysophosphatidic acid in a plasma sample of the patient.

The preferred method comprises: providing a blood specimen from the patient, obtaining a blood plasma sample which is substantially free of platelets from the blood specimen, preparing a lipid extract from said plasma sample, and detecting the presence of lysophosphatidic acid in said lipid extract. Because the method is sufficiently sensitive to detect ovarian carcinoma in subjects with early stage ovarian carcinoma, sufficiently specific to distinguish benign gynecological carcinomas from malignant gynecological carcinomas, and marginally invasive, the method is especially useful for screening patients for ovarian carcinomas.

The method also detects the presence of endometrial carcinoma, peritoneal carcinoma, and cervical carcinoma in a subject. Accordingly, the method is useful for screening for more than one gynecological carcinoma.

A new method for extracting lysophosphatidic acid from a biological fluid is also provided. The method which comprises acidifying the biological fluid and extracting the lysophosphatidic acid from the acidified sample with an organic solvent is useful for extracting greater than 80% of the lysophosphatidic acid in the biological fluid.

DETAILED DESCRIPTION OF THE INVENTION

The present invention provides a new, simple method for detecting the presence of a gynecological carcinoma particularly ovarian carcinomas in a patient. The method comprises detecting the presence of lysophosphatidic acid in a blood plasma sample from the patient. Preferably, the blood plasma sample is substantially free of platelets. As described herein, a plasma sample is substantially free of platelets when it contains less than 95% of the platelets present in the original blood specimen obtained from the patient. In a preferred embodiment, the method comprises providing a whole blood specimen from the patient, obtaining a plasma sample which is substantially free of platelets from the whole blood specimen, extracting lipids from the blood plasma sample, and detecting the presence of lysophosphatidic acid in the lipid extract.

Preferably, the blood plasma sample is obtained under conditions which minimize the release of lysophosphatidic acid from platelets which are present in the whole blood specimen. Such conditions include, for example, collecting the whole blood specimen from the subject in tubes that contain an anti-coagulant. Suitable anti-coagulants include, for example, heparin and chelating agents. It is preferred that the whole blood specimen be collected in the presence of a chelating agent, such as for example ethylenediaminetetraacetic acid (EDTA) or sodium citrate, more preferably EDTA, since chelating agents both reduce phospholipase activity in the sample and prevent clotting of the whole blood specimen.

The blood plasma typically is obtained by centrifuging the whole blood specimen to pellet the blood cells in the whole blood specimen and collecting the supernatant, which represents the major portion of the blood plasma in the whole blood specimen.

Preferably, the blood plasma is obtained from the blood specimen by a procedure which comprises a first centrifugation step to provide a pellet of blood cells and platelets and a first supernatant and a second centrifugation step wherein the first supernatant is centrifuged to provide a second pellet of platelets and a plasma supernatant. Preferably the speed of the first centrifugation step is between 400 to 1000×g, more preferably from about 500 to 650×g, most preferably from about 550 to about 600×g. The supernatant is then removed from the tube and centrifuged a second time at a speed of between 6500 to 10000×g, more preferably from about 7000 to 8500×g. The two-step centrifugation procedure minimizes the release of lysophosphatidic acid from platelets and thus permits a more accurate determination of lysophosphatidic acid in the sample.

Substantially all of the lipids, particularly the phospholipids, in the plasma sample are then extracted, preferably by a lipid extraction procedure which recovers at least 80% of the lysophosphatidic acid from the plasma sample. More preferably, the lipid extraction procedure recovers at least 85% of the LPA in the plasma sample. An example of a preferred lipid extraction procedure comprises the steps of: acidifying the blood plasma sample; mixing the acidified blood plasma sample with an organic solvent to provide an aqueous phase and an organic phase, wherein the phospholipids preferentially distribute to the organic phase; and recovering the organic phase to provide a lipid extract which contains greater than 80% of the lysophosphatidic acid in the plasma sample. Preferably, hydrochloric acid is used to acidify the blood plasma sample. Preferably the final concentration of acid in the acidified plasma sample is from about 0.2 N to about 2.0 N, more preferably from about 1.3 N to about 2.0 N.

Suitable organic solvents for extracting lysophosphatidic acid from the acidified plasma sample include for example butanol, isopropanol, and mixed organic solvents which comprise a polar organic solvent, such as for example methanol, and a non-polar organic solvent, such as for example chloroform. Preferably the organic solvent is a mixture of methanol and chloroform at a 2:1 ratio.

The lysophosphatidic acid, also referred to herein as "LPA," is then separated from the other phospholipids in the organic phase using conventional techniques, such as for example, separation by thin-layer chromatography. Preliminary studies in which standards including lysophosphatidylcholine, lysophosphatidylinositol, lysophosphatidylserine, lysophosphatidylethanolamine, and the lysophosphatidic acids, palmitoyl-LPA, oleoyl-LPA and stearoyl-LPA were separated by one-dimensional TLC indicated that the Rf value of LPA was 0.14 for palmitoyl and stearoyl LPA and 0.13 for oleoyl-LPA. The preliminary studies also indicated that each of the LPA species migrated at a rate slower than that of lysophosphatidylcholine and at a rate different from lysophosphatidylinositol, lysophosphatidylserine, and lysophosphatidylethanolamine. Preliminary studies in which the phospholipid standards were subjected to two-dimensional TLC also indicated that LPA prepared in this manner, i.e. by one-dimensional TLC, does not contain any other phospholipids.

The amount of lysophosphatidic acid in the LPA fraction is then quantified using conventional techniques. The quantification technique used depends upon the amount of blood specimen provided by the subject. For example, if the size of the blood specimen is 2 ml or less, it is preferred that a quantification technique which is capable of detecting picomole amounts of LPA be used. Suitable techniques for detecting picomole amounts of LPA include, for example, hydrolyzing the isolated LPA fraction and then quantifying the amount of each fatty acid in the hydrolysate by gas chromatography. If the size of the blood specimen is 20 ml or greater, a technique which is capable of detecting nanomole amounts of LPA, such as for example total phosphorous determination in the LPA fraction, is suitable.

The methods disclosed herein are useful for detecting gynecological carcinomas such as cervical carcinoma, endometrial carcinoma, peritoneal carcinoma, and ovarian carcinoma, that is, epithelial ovarian cancer. Epithelial ovarian cancer includes serous tumors, mucinous tumors, endometroid tumors, clear cell tumors, undifferentiated carcinoma, mixed epithelial tumors, and unclassified epithelial tumors.

The methods disclosed herein are especially useful for assessing the malignancy of an ovarian mass in a patient and for detecting ovarian carcinomas at the early surgical stage of development in a patient, that is Surgical Stage I and Surgical Stage II, as well as at the later stages of development, that is Surgical Stage III and Surgical Stage IV. Surgical stage represents the severity of disease with Stage I being least severe and Stage IV being the most severe. According to criteria established by the International Federation of Gynecology and Obstetrics, the ovarian carcinoma is limited to the ovaries and may or may not include ascites in Stage I ovarian carcinoma. In Stage II, there is pelvic extension of the carcinoma and possibly extension to the uterus or fallopian tubes. Stage III ovarian carcinoma is characterized by abdominal metastases. In Stage IV, there is distant metastases of the carcinoma outside of the peritoneal cavity.

The methods disclosed herein are simple, marginally invasive, and require only a blood specimen from the subject. Thus, such methods are also useful for screening patients who have not been previously diagnosed as carrying carcinoma, particularly patients who are at risk for gynecological carcinomas, especially ovarian carcinoma. Such patients include women at elevated risk by virtue of a family history of the disease, premenopausal women with anovulatory cycles, and postmenopausal women.

The present invention is further described by the examples which follow. Such examples, however, are not to be construed as limiting in any way either the spirit or the scope of the present invention.

EXAMPLE

Plasma samples were obtained from blood specimens provided by eighty-four female subjects. A whole blood specimen of approximately 2 ml was collected from each of the subjects in a 5 ml vacutainer tube containing 7.2 mg of EDTA.

Obtaining a Plasma Sample from the whole blood specimen

The whole blood specimen was centrifuged at 580×g for 5 minutes to provide a pellet of the blood cells and platelets and a supernatant. The supernatant was transferred to a siliconized microcentrifuge tube and centrifuged for 5 minutes at 8000×g to provide a second pellet and a plasma supernatant. The plasma supernatant was either processed immediately or stored at −70° C.

Extracting LPA from a Plasma Sample.

Extraction of lipids, particularly LPA from the plasma sample was performed at 0–4° C. Each 1 mL sample of plasma was acidified by adding 0.2 mL of 12 N HCl to provide a plasma sample with a final concentration of HCl of approximately 2.0 N. After mixing, 4 mL of mixed organic solvent comprising a 2:1 ratio of methanol/chloroform was added to the acidified plasma and the mixture was vortexed for 1 minute and incubated on ice for 10 minutes. 1 mL of chloroform and 1.25 mL of $H_2O$ were added to the mixture. After mixing thoroughly, the mixture was centrifuged at 1000×g for 10 minutes at 4° C. The lower organic layer was transferred to a new glass tube and dried at 40° C. under nitrogen to provide a phospholipid extract.

The total recovery rate and reproducibility of this extraction procedure was examined by adding 10 nmol of synthetic oleoyl-LPA to three parallel plasma samples lacking endogenous oleoyl-LPA. The samples were extracted by the present procedure and the amount of oleoyl-LPA in each sample quantified. This analysis indicated that the average recovery of LPA by the present extraction procedure was 92.7% with a standard error of ±5.6%.

Isolating the LPA in the Lipid Extract

Each lipid extract was dissolved in 50 μl of a 2:1 methanol/chloroform mixture and loaded onto a single lane of a precoated silica-gel 60 TLC plate (20×20 cm, layer thickness 250 mm) obtained from EM Science, Darmstadt, Germany. A 50 μl aliquot of a 2:1 methanol/chloroform mixture containing 10 to 50 μg of oleoyl-LPA obtained from Avanti Polar-Lipids, Inc. was loaded onto one outside lane of the plate and a 50 μl aliquot of chloroform containing 10 to 50 μg of lysophosphatidylcholine obtained from Sigma Chemical Company was loaded onto the opposite outside lane of the plate. The oleoyl-LPA and lysophosphatidylcholine were used as migration references for locating the LPA fractions on the plate. The lipids were developed at room temperature for approximately 3 hours with a mixture of chloroform-methanol-ammonium hydroxide (65:35:5.5). Then the outside lanes containing the oleoyl LPA and lysophosphatidylcholine standards were sprayed with 0.1% 8-anilino-1-naphthalene-sulfonic acid and visualized under ultraviolet light.

Each of the isolated LPA fractions in the lanes loaded with lipid extracts from the plasma samples were scraped from the plates into separate 15 mL disposable glass centrifuge tubes from Kimble, Vineland, N.J. The LPA fractions included all of the lipids that migrated to a distance on the plate which corresponded to the Rf of the oleolyl-LPA standard and extended to but was less than the Rf of the lysophosphatidylcholine standard.

Measuring the Amount of LPA Isolated from Each Sample 2 mL of 1M ethanolic KOH were added to each tube containing the isolated LPA fractions. The tubes were then incubated at 60° C. for 1 hour to hydrolyze the LPA present in the tube. After cooling, 5 μl of internal standard solution contains methyl behenate, 1.5 mg/mL in chloroform, 1 mL of 6N HCl, 5 mL of $H_2O$ and 5 mL of ethyl ether were added to the hydrolysate. The mixture was vortexed for 30 seconds and centrifuged at 1000×g for 10 minutes. Then, the upper layer was transferred into a new glass tube and dried at 40° C. under nitrogen. The residue, which contained fatty acids released from the LPA, was dissolved in 0.6 mL of petroleum ether and the dissolved fatty acids were transmethylated by adding 1 mL of $BCl_3$-methanol reagent to each tube and incubating at 100° C. for 10 minutes. $BCl_3$ methanol was obtained from Supelco Inc., Bellefonte, Pa. The fatty acid methyl esters were extracted with 1 ml of petroleum ether. The mixture was vortexed for 10 seconds and centrifuged at 1000×g for 5 minutes. The top layer was transferred to a 3.7 mL screw-topped Supelco sample vial and dried at 40° C. under nitrogen. The residue was then dissolved in 25 μl of chloroform and 5–15 μl of the chloroform solution was used for analysis by gas chromatography.

GC analysis of the Fatty Acids Released from LPA by Hydrolysis

A Hewlett-Packard Model 5710A gas chromatograph, equipped with a fused silica column (25 m×0.2 mm) coated with 3% SP-2310, 2% SP-2300 on 100/120 Chromosorb WAW from Supelco Inc., was used to measure the amount of each fatty acid in each of the samples. The gas chromatograph conditions were as follows: the oven starting temperature was 185° C.; after 2 minutes, the temperature was increased at 2° C./minutes to 230° C., and held for 4 minutes; the injector temperature was 200° C.; the detector temperature was 300° C.; nitrogen was the carrier gas at a flow rate of 30 ml/minutes at 50 PSI; air flow rate was 240 ml/minutes at 24 PSI; hydrogen flow was 30 ml/min at 15 Psi. A flame ionization detector was used to detect the fatty acid methyl esters. Two standard curves were obtained using two fatty acid methyl esters standard mixtures obtained from Nu Check Prep. Inc., Elysian, Minn. The two standard mixtures included different combinations of the esters of methyl palmitate, methyl stearate, methyl oleate, methyl linoleate, methyl arachidonate and methyl behanate. The retention times were 3.8 min for methyl palmitate, 6.7 min for methyl stearate, 7.3 min for methyl oleate, 8.3 min for methyl linoleate, 14.0 min for methyl arachidonate and 15.3 min for methyl behenate (internal standard).

The concentrations of each fatty acid in each sample were calculated and added together to obtain the concentration of total LPA in each plasma sample. The concentrations in μM of each LPA species and of total LPA in each of the samples are presented in Table I.

Each of the female subjects also underwent one or more routine diagnostic procedures to determine whether she was healthy or had an active disease. The diagnostic procedures included, where appropriate, clinical examination, clinical chemistries, and surgical evaluation of any masses detected. On the basis of these routine diagnostic procedures, the patients were diagnosed as being healthy or as having an active form of one of the diseases listed in Table I.

TABLE I

LPA Levels (μM) in Plasma of Subjects of the Example

| Diagnosis | LPA(P) | LPA(S) | LPA(O) | LPA(L) | LPA(A) | LPA(D) | TOTAL LPA |
|---|---|---|---|---|---|---|---|
| 1. Ovarian Carcinoma Stage I | | | | | | | |
| #1 | 9.97 | 12.84 | 4.39 | 2.83 | 2.29 | B.D. | 32.32 |
| #2 | 10.78 | 10.28 | 1.84 | B.D. | B.D. | B.D. | 22.9 |
| #3 | 1.39 | 0.40 | 0.87 | 2.01 | B.D. | B.D. | 4.67 |
| 2. Ovarian Carcinoma Stage II | | | | | | | |
| #1 | 0.78 | 2.17 | 0.68 | 0.98 | 0.41 | B.D. | 5.02 |

TABLE I-continued

LPA Levels (μM) in Plasma of Subjects of the Example

| Diagnosis | LPA(P) | LPA(S) | LPA(O) | LPA(L) | LPA(A) | LPA(D) | TOTAL LPA |
|---|---|---|---|---|---|---|---|
| 3. Ovarian Carcinoma Stage III | | | | | | | |
| #1 | 8.87 | 9.15 | 3.98 | 4.17 | 3.32 | B.D. | 29.49 |
| #2 | 7.90 | 6.97 | 3.46 | 8.97 | 6.45 | B.D. | 33.75 |
| #3 | 9.59 | 6.96 | 1.59 | 1.64 | 2.56 | B.D. | 22.34 |
| #4 | 11.09 | 7.62 | 5.72 | 11.78 | 6.85 | B.D. | 43.06 |
| #5 | 5.64 | 4.14 | B.D. | B.D. | B.D. | B.D. | 9.78 |
| #6 | 3.10 | 4.62 | 1.58 | 3.18 | 1.59 | B.D. | 14.07 |
| #7 | 2.13 | 1.80 | 0.39 | 0.91 | B.D. | B.D. | 5.23 |
| #8 | 0.81 | 1.56 | 0.77 | B.D. | B.D. | B.D. | 3.14 |
| #9 | 3.30 | 6.22 | 2.28 | 5.40 | 5.17 | B.D. | 22.37 |
| #10 | 2.37 | 4.33 | 1.56 | 0.77 | 0.92 | B.D. | 9.95 |
| #11 | 5.34 | 8.32 | 2.68 | 1.85 | 2.39 | B.D. | 20.58 |
| #12 | 8.97 | 10.23 | 11.39 | 13.50 | 8.96 | 3.12 | 56.17 |
| #13 | 1.08 | 0.89 | 0.31 | 0.25 | B.D. | B.D. | 2.53 |
| #14 | B.D. | 1.82 | 0.43 | 2.42 | 2.42 | B.D. | 5.84 |
| 4. Ovarian Carcinoma Stage IV | | | | | | | |
| #1 | 3.61 | 4.91 | 2.09 | 1.16 | B.D. | B.D. | 11.77 |
| 5. Peritoneal Carcinoma | | | | | | | |
| #1 | 14.22 | 9.93 | 3.08 | 3.79 | 1.94 | B.D. | 32.96 |
| #2 | 3.19 | 6.29 | 0.68 | 6.25 | B.D. | B.D. | 16.41 |
| #3 | 2.65 | 2.29 | 0.13 | B.D. | B.D. | B.D. | 5.07 |
| #4 | 12.81 | 11.45 | 12.50 | 14.92 | 9.19 | 2.34 | 63.21 |
| #5 | 0.70 | 1.17 | B.D. | B.D. | B.D. | B.D. | 1.87 |
| #6 | B.D. | B.D. | B.D. | B.D. | B.D. | B.D. | B.D. |
| #7 | 3.89 | 4.01 | 3.94 | 4.51 | 2.84 | B.D. | 19.19 |
| #8 | 3.11 | 3.15 | 1.72 | 2.40 | 1.70 | B.D. | 12.08 |
| #9 | 1.16 | B.D. | B.D. | B.D. | 0.28 | B.D. | 1.44 |
| 6. Endometrial Carcinoma | | | | | | | |
| #1 | 8.46 | 9.45 | 3.85 | 4.83 | 2.23 | B.D. | 28.82 |
| #2 | 11.01 | 11.31 | 2.33 | 1.03 | B.D. | B.D. | 25.68 |
| #3 | 6.84 | 15.84 | 12.62 | 18.88 | 9.05 | B.D. | 63.23 |
| #4 | 7.68 | 7.27 | 3.53 | 5.67 | 7.24 | B.D. | 31.39 |
| #5 | 1.71 | 1.65 | 0.59 | B.D. | B.D. | B.D. | 3.95 |
| #6 | 6.19 | 7.65 | 2.59 | 5.27 | 2.89 | B.D. | 24.59 |
| #7 | 21.15 | 5.16 | 16.41 | 20.98 | B.D. | B.D. | 54.56 |
| 7. Cervical Carcinoma | | | | | | | |
| #1 | 5.94 | 5.60 | 2.99 | 1.19 | 2.10 | B.D. | 17.82 |
| #2 | 12.45 | 11.18 | 6.72 | 10.44 | 6.53 | B.D. | 47.32 |
| #3 | 0.86 | 1.14 | B.D. | B.D. | B.D. | B.D. | 2.00 |
| #4 | 15.29 | 12.98 | 8.27 | 5.68 | 8.97 | B.D. | B.D. |
| 8. Healthy | | | | | | | |
| #1 | B.D. | B.D. | B.D. | B.D. | B.D. | B.D. | B.D. |
| #2 | B.D. | B.D. | 0.42 | B.D. | B.D. | B.D. | 0.42 |
| #3 | B.D. | B.D. | B.D. | B.D. | B.D. | B.D. | B.D. |
| #4 | B.D. | B.D. | B.D. | B.D. | B.D. | B.D. | B.D. |
| #5 | B.D. | B.D. | B.D. | B.D. | B.D. | B.D. | B.D. |
| #6 | B.D. | 1.94 | 0.21 | B.D. | B.D. | B.D. | 2.15 |
| #7 | B.D. | B.D. | B.D. | B.D. | B.D. | B.D. | B.D. |
| #8 | B.D. | B.D. | B.D. | B.D. | B.D. | B.D. | B.D. |
| #9 | B.D. | B.D. | B.D. | B.D. | B.D. | B.D. | B.D. |
| #10 | B.D. | B.D. | B.D. | B.D. | B.D. | B.D. | B.D. |
| #11 | B.D. | B.D. | B.D. | B.D. | B.D. | B.D. | B.D. |
| #12 | B.D. | B.D. | B.D. | B.D. | B.D. | B.D. | B.D. |
| #13 | B.D. | B.D. | 0.42 | B.D. | B.D. | B.D. | 0.42 |
| #14 | B.D. | B.D. | B.D. | B.D. | B.D. | B.D. | B.D. |
| #15 | B.D. | B.D. | B.D. | B.D. | B.D. | B.D. | B.D. |
| #16 | B.D. | B.D. | B.D. | B.D. | B.D. | B.D. | B.D. |
| #17 | 0.48 | 0.69 | B.D. | B.D. | B.D. | B.D. | 1.17 |
| #18 | B.D. | B.D. | B.D. | B.D. | B.D. | B.D. | B.D. |
| #19 | B.D. | B.D. | B.D. | B.D. | B.D. | B.D. | B.D. |
| #20 | B.D. | B.D. | B.D. | B.D. | B.D. | B.D. | B.D. |
| #21 | B.D. | B.D. | B.D. | B.D. | B.D. | B.D. | B.D. |
| #22 | 4.93 | B.D. | B.D. | B.D. | B.D. | B.D. | 4.93 |

TABLE I-continued

LPA Levels (μM) in Plasma of Subjects of the Example

| Diagnosis | LPA(P) | LPA(S) | LPA(O) | LPA(L) | LPA(A) | LPA(D) | TOTAL LPA |
|---|---|---|---|---|---|---|---|
| #23 | B.D. | B.D. | B.D. | B.D. | B.D. | B.D. | B.D. |
| 9. Benign GYN Diseases | | | | | | | |
| #1 | B.D. | B.D. | B.D. | B.D. | B.D. | B.D. | B.D. |
| #2 | B.D. | B.D. | B.D. | B.D. | B.D. | B.D. | B.D. |
| #3 | B.D. | B.D. | B.D. | B.D. | B.D. | B.D. | B.D. |
| 10. Sarcoma | | | | | | | |
| #1 | B.D. | B.D. | B.D. | B.D. | B.D. | B.D. | B.D. |
| #2 | B.D. | B.D. | B.D. | B.D. | B.D. | B.D. | B.D. |
| #3 | B.D. | B.D. | B.D. | B.D. | B.D. | B.D. | B.D. |
| #4 | B.D. | 2.08 | 0.99 | 1.43 | 3.48 | B.D. | 7.97 |
| 11. Breast Cancer | | | | | | | |
| #1 | B.D. | B.D. | B.D. | B.D. | B.D. | B.D. | B.D. |
| #2 | B.D. | B.D. | 0.42 | B.D. | B.D. | B.D. | 0.42 |
| #3 | B.D. | B.D. | B.D. | B.D. | B.D. | B.D. | B.D. |
| #4 | B.D. | B.D. | B.D. | B.D. | B.D. | B.D. | B.D. |
| #5 | B.D. | B.D. | B.D. | B.D. | B.D. | B.D. | B.D. |
| #6 | B.D. | B.D. | B.D. | B.D. | B.D. | B.D. | B.D. |
| #7 | B.D. | B.D. | B.D. | B.D. | B.D. | B.D. | B.D. |
| #8 | B.D. | B.D. | B.D. | B.D. | B.D. | B.D. | B.D. |
| #9 | B.D. | B.D. | B.D. | B.D. | B.D. | B.D. | B.D. |
| #10 | B.D. | B.D. | B.D. | B.D. | B.D. | B.D. | B.D. |
| #11 | B.D. | B.D. | B.D. | B.D. | B.D. | B.D. | B.D. |
| 12. Leukemia | | | | | | | |
| #1 | B.D. | B.D. | B.D. | B.D. | B.D. | B.D. | B.D. |
| #2 | B.D. | B.D. | B.D. | B.D. | B.D. | B.D. | B.D. |
| #3 | B.D. | B.D. | B.D. | B.D. | B.D. | B.D. | B.D. |
| #4 | B.D. | B.D. | B.D. | B.D. | B.D. | B.D. | B.D. |

LPA(P): palmitoyl - LPA
LPA(S): stearoyl - LPA
LPA(O): oleoyl - LPA
LPA(L): linolenyl - LPA
LPA(A): arachidyl - LPA
LPA(D): docosahexanyl - LPA
B.D.: below detection
N.A.: Not available The average concentrations ±SE of each LPA species in the plasma of patients diagnosed as having a gynecological carcinoma and the average concentration ±SE of each LPA species in the plasma of patients diagnosed as not having a gynecological carcinoma are presented in Table II. The average concentrations ±SE of total LPA in the plasma of patients with the gynecological carcinomas and the average concentrations ±SE of total LPA in the plasma of patients without gynecological carcinomas are presented in Table III. The statistical power calculations were performed using the Wilcoxon Rank Sum statistical test as described by W. J. Conover in Practical Nonparametric. 0.1 μm was used in calculations where LPA levels were below detection.

TABLE II

Average Concentration of Individual LPA Species in the Plasma of Subjects from the Example

| Diagnosis | N | LPA | Mean | SE | SD | Median | Min | Max |
|---|---|---|---|---|---|---|---|---|
| Healthy | 23 | LPA(P) | 0.33 | 0.21 | 1.01 | 0.10 | 0.10 | 4.93 |
| | | LPA(S) | 0.21 | 0.08 | 0.40 | 0.10 | 0.10 | 1.94 |
| | | LPA(O) | 0.10 | 0.00 | 0.02 | 0.10 | 0.10 | 0.21 |
| | | LPA(L) | 0.10 | 0.00 | 0.00 | 0.10 | 0.10 | 0.10 |
| | | LPA(A) | 0.10 | 0.00 | 0.00 | 0.10 | 0.10 | 0.10 |
| | | LPA(D) | 0.10 | 0.00 | 0.00 | 0.10 | 0.10 | 0.10 |
| Ovarian Carcinoma | 19 | LPA(P) | 5.10 | 0.88 | 3.85 | 3.61 | 0.10 | 11.09 |
| | | LPA(S) | 5.54 | 0.83 | 3.61 | 4.91 | 0.40 | 12.84 |
| | | LPA(O) | 2.43 | 0.61 | 2.66 | 1.59 | 0.10 | 11.39 |
| | | LPA(L) | 3.27 | 0.91 | 3.96 | 1.85 | 0.10 | 13.50 |
| | | LPA(A) | 2.32 | 0.62 | 2.70 | 1.59 | 0.10 | 8.96 |
| | | LPA(D) | 0.26 | 0.16 | 0.69 | 0.10 | 0.10 | 3.12 |
| Peritoneal Carcinoma | 9 | LPA(P) | 4.65 | 1.73 | 5.19 | 3.11 | 0.10 | 14.22 |
| | | LPA(S) | 4.28 | 1.38 | 4.14 | 3.15 | 0.10 | 11.45 |
| | | LPA(O) | 2.48 | 1.34 | 4.02 | 0.68 | 0.10 | 12.50 |
| | | LPA(L) | 3.59 | 1.61 | 4.83 | 2.40 | 0.10 | 14.92 |
| | | LPA(A) | 1.82 | 0.98 | 2.95 | 0.28 | 0.10 | 9.19 |
| | | LPA(D) | 0.35 | 0.25 | 0.75 | 0.10 | 0.10 | 2.34 |
| Endo-metrial Carcinoma | 7 | LPA(P) | 9.01 | 2.29 | 6.05 | 7.68 | 1.71 | 21.15 |
| | | LPA(S) | 8.33 | 1.71 | 4.52 | 7.65 | 1.65 | 15.84 |
| | | LPA(O) | 5.99 | 2.27 | 6.02 | 3.53 | 0.59 | 16.41 |
| | | LPA(L) | 8.11 | 3.16 | 8.37 | 5.27 | 0.10 | 20.98 |
| | | LPA(A) | 3.10 | 1.38 | 3.66 | 2.23 | 0.10 | 9.05 |
| | | LPA(D) | 0.10 | 0.00 | 0.00 | 0.10 | 0.10 | 0.10 |
| Cervical Carcinoma | 4 | LPA(P) | 8.64 | 3.25 | 6.50 | 9.20 | 0.86 | 15.29 |
| | | LPA(S) | 7.73 | 2.70 | 5.40 | 8.39 | 1.14 | 12.98 |
| | | LPA(O) | 4.52 | 1.84 | 3.69 | 4.86 | 0.10 | 8.27 |
| | | LPA(L) | 4.35 | 2.36 | 4.72 | 3.44 | 0.10 | 10.44 |

TABLE II-continued

Average Concentration of Individual LPA Species
in the Plasma of Subjects from the Example

| Diagnosis | N | LPA | Mean | SE | SD | Median | Min | Max |
|---|---|---|---|---|---|---|---|---|
| | | LPA(A) | 4.43 | 2.02 | 4.05 | 4.32 | 0.10 | 8.97 |
| | | LPA(D) | 0.10 | 0.00 | 0.00 | 0.10 | 0.10 | 0.10 |
| Benign | 3 | LPA(P) | 0.10 | 0.00 | 0.00 | 0.10 | 0.10 | 0.10 |
| Gyneco- | | LPA(S) | 0.10 | 0.00 | 0.00 | 0.10 | 0.10 | 0.10 |
| logical | | LPA(O) | 0.10 | 0.00 | 0.00 | 0.10 | 0.10 | 0.10 |
| Disease | | LPA(L) | 0.10 | 0.00 | 0.00 | 0.10 | 0.10 | 0.10 |
| | | LPA(A) | 0.10 | 0.00 | 0.00 | 0.10 | 0.10 | 0.10 |
| | | LPA(D) | 0.10 | 0.00 | 0.00 | 0.10 | 0.10 | 0.10 |
| Sarcoma | 4 | LPA(P) | 0.10 | 0.00 | 0.00 | 0.10 | 0.10 | 0.10 |
| | | LPA(S) | 0.60 | 0.50 | 0.99 | 0.10 | 0.10 | 2.08 |
| | | LPA(O) | 0.32 | 0.22 | 0.45 | 0.10 | 0.10 | 0.99 |
| | | LPA(L) | 0.43 | 0.33 | 0.67 | 0.10 | 0.10 | 1.43 |
| | | LPA(A) | 0.95 | 0.85 | 1.69 | 0.10 | 0.10 | 3.48 |
| | | LPA(D) | 0.10 | 0.00 | 0.00 | 0.10 | 0.10 | 0.10 |
| Breast | 11 | LPA(P) | 0.10 | 0.00 | 0.00 | 0.10 | 0.10 | 0.10 |
| Cancer | | LPA(S) | 0.10 | 0.00 | 0.00 | 0.10 | 0.10 | 0.10 |
| | | LPA(O) | 0.18 | 0.03 | 0.10 | 0.10 | 0.10 | 0.43 |
| | | LPA(L) | 0.10 | 0.00 | 0.00 | 0.10 | 0.10 | 0.10 |
| | | LPA(A) | 0.10 | 0.00 | 0.00 | 0.10 | 0.10 | 0.10 |
| | | LPA(D) | 0.10 | 0.00 | 0.00 | 0.10 | 0.10 | 0.10 |
| Leukemia | 4 | LPA(P) | 0.10 | 0.00 | 0.00 | 0.10 | 0.10 | 0.10 |
| | | LPA(S) | 0.10 | 0.00 | 0.00 | 0.10 | 0.10 | 0.10 |
| | | LPA(0) | 0.10 | 0.00 | 0.00 | 0.10 | 0.10 | 0.10 |
| | | LPA(L) | 0.10 | 0.00 | 0.00 | 0.10 | 0.10 | 0.10 |
| | | LPA(A) | 0.10 | 0.00 | 0.00 | 0.10 | 0.10 | 0.10 |
| | | LPA(D) | 0.10 | 0.00 | 0.00 | 0.10 | 0.10 | 0.10 |

LPA(P): palmitoyl - LPA
LPA(S): stearoyl - LPA
LPA(O): oleoyl - LPA
LPA(L): linolenyl - LPA
LPA(A): arachidyl - LPA
LPA(D): docosahexanyl - LPA
B.D.: below detection
N.A.: Not available

TABLE III

Average Concentration of Total LPA ($\mu$M) in the Plasma of Patients

| Diagnosis | N | Mean | SE | SD | Median | Min | Max |
|---|---|---|---|---|---|---|---|
| Healthy | 23 | 0.45 | 0.23 | 1.09 | 0.10 | 0.10 | 4.93 |
| Ovarian Carcinoma | 19 | 18.68 | 3.43 | 14.97 | 14.07 | 2.53 | 56.17 |
| Peritoneal Carcinoma | 9 | 16.93 | 6.79 | 20.37 | 12.08 | 0.10 | 63.21 |
| Endometrial Carcinoma | 7 | 33.17 | 7.51 | 19.86 | 28.82 | 3.95 | 63.23 |
| Cervical Carcinoma | 4 | 29.58 | 11.83 | 23.67 | 32.57 | 2.00 | 51.19 |
| Benign Gynecological Disease | 3 | 0.10 | 0.00 | 0.00 | 0.10 | 0.10 | 0.10 |
| Sarcoma | 4 | 4.83 | 1.05 | 5.04 | 3.62 | 0.10 | 19.92 |
| Breast Cancer | 11 | 0.13 | 0.03 | 0.10 | 0.10 | 0.10 | 0.43 |
| Leukemia | 4 | 0.10 | 0.00 | 0.00 | 0.10 | 0.10 | 0.10 |

LPA(P): palmitoyl - LPA
LPA(S): stearoyl - LPA
LPA(O): oleoyl - LPA
LPA(L): linolenyl - LPA
LPA(A): arachidyl - LPA
LPA(D): docosahexanyl - LPA
B.D.: below detection
N.A.: Not available As shown in Table I, detectable levels of total LPA were found in each of the patients with Stage I, Stage II, Stage III or Stage IV ovarian carcinoma. Thus, every one of the patients diagnosed as having early stage ovarian carcinoma or late state ovarian carcinoma had detectable levels of LPA in her plasma. No false negatives were observed in any of the patients with ovarian carcinoma. The concentration of total LPA in subjects with Stage I and Stage II ovarian carcinoma ranged from 4.67 to 32.32 $\mu$M. The concentration of total LPA in subjects with Stage III and Stage IV carcinoma ranged from 2.53 to 56.17 $\mu$M. Moreover, detectable levels of stearoyl-LPA were found in all of the patients with ovarian carcinoma and detectable levels of the LPA species palmitoyl-LPA and oleoyl-LPA were found in 18 out of the 19 patients with ovarian carcinoma.

In contrast, 19 out of the 23 subjects who were characterized as being healthy, did not have detectable levels of LPA in their plasma. The remaining four healthy patients had low concentrations of LPA in their plasma, ranging from 0.42 to 4.93 $\mu$M. It is not known whether these values represent false positives or whether these individuals had a gynecological carcinoma that was not detected by the other routine procedures used to diagnose the patients. Moreover, the average concentration of total LPA and of each LPA species in the plasma of patients diagnosed as having ovarian carcinoma was significantly higher than the average concentration of total LPA and of each LPA-species in the plasma of healthy patients. These results establish that the present method is highly sensitive and therefore useful for identifying those patients with the gynecological carcinoma of ovarian carcinoma, including those patients whose ovarian carcinomas are still in the early stages of development. The results also indicate that a method which detects the presence of palmitoyl LPA or stearoyl-LPA or oleoyl-LPA or combinations thereof in the plasma of patients is also useful for detecting ovarian carcinomas.

LPA was also detected in the plasma of every one of the subjects diagnosed as having cervical carcinoma and endometrial carcinoma, and in eight out of the nine subjects diagnosed as having peritoneal carcinoma. The peritoneal carcinoma had been totally debulked in the one patient who did not have detectable levels of LPA in her plasma. This result suggests that LPA is not present in the plasma of patients whose carcinomas are completely removed by surgery. Thus, the present method is useful for monitoring the recurrence of gynecological carcinomas in patients who have undergone surgical removal of the carcinoma. The concentration of LPA in the plasma of the subjects with cervical carcinoma and endometrial carcinoma ranged from 2.00 to 63.23 $\mu$M.

In contrast, detectable levels of LPA were not present in 15 out of the 17 patients diagnosed as having a cancer other than a gynecological carcinoma, i.e., breast cancer, leukemia, and uterine sarcoma. Moreover, detectable levels of LPA were not present in any of the subjects with uterine fibroids, a benign gynecological disease. Since plasma from three out of the four patients with gynecological sarcomas, which are derived from connective tissues, and with benign uterine fibroids did not have detectable levels of total LPA in their plasma, it is believed that malignant epithelial cells of the respective gynecological organ may be the source of the LPA in the plasma of patients with ovarian carcinoma, cervical carcinoma, endometrial carcinoma, and peritoneal carcinoma.

Because of its sensitivity, simplicity, and low cost, the present method is useful for screening patients for gynecological carcinomas. Because the blood specimens for the present method and for CA 125 testing can be drawn from a patient at the same time, CA 125 testing can also be performed when patients are screened for gynecological carcinomas by the present methods. Alternatively, the present method can be used alone to detect gynecological carcinomas.

Because the LPA is not present in the plasma of patients with benign gynecological diseases, the present method is also useful for distinguishing between gynecological diseases which are benign and gynecological diseases which are malignant in patients with gynecological masses. Use of this method to discriminate between malignant and benign ovarian masses should reduce the number of patients required to undergo the more expensive techniques such as transvaginal sonography or the more invasive techniques such as tumor biopsy or tumor aspiration that are now used to diagnose ovarian tumor malignancy.

Although the invention has been described with regard to a number of preferred embodiments, which constitute the best mode presently known to the inventors for carrying out this invention, it should be understood that various changes and modifications as would be obvious to one having the ordinary skill in this art may be made without departing from the scope of the invention which is defined by the claims which are appended hereto.

What is claimed:

1. A method for diagnosing the presence of ovarian carcinoma in a subject comprising the following steps:
    (a) preparing a plasma sample from a blood specimen collected from the subject;
    (b) preparing a lipid extract from said plasma sample;
    (c) testing for the presence of lysophosphatidic acid in said lipid extract; and
    (d) correlating the presence of lysophosphatidic acid in said lipid extract with the presence of said ovarian carcinoma in said subject.

2. The method of claim 1 wherein said plasma sample is prepared from said blood specimen by a process which comprises the following steps:
    (a) centrifuging said blood specimen at a first speed of between 400×g and 1000×g to obtain a first pellet of blood cells and platelets and a first supernatant; and
    (b) centrifuging the first supernatant of step (a) at a second speed of between 6500 and 10000×g to obtain a second pellet and a second supernatant;
    (c) collecting said second supernatant from step (b) to provide said plasma sample.

3. The method of claim 1 wherein the presence of lysophosphatidic acid in said lipid extract is detected by a process which comprises the following steps:
    (a) separating the lipid extract into phospholipid fractions; and
    (b) detecting the presence of lysophosphatidic acid in said phospholipid fractions.

4. The method of claim 1 wherein the testing for the presence of lysophosphatidic acid in said lipid extract is a process which comprises the following steps:
    (a) isolating a plurality of phospholipid fractions from said lipid;
    (b) testing for the presence of palmitoyl-lysophosphatidic acid, or stearoyl-lysophosphatidic acid, or oleoyl-lysophosphatidic acid, or combinations thereof in said phospholipid fractions; and
    (c) correlating the presence of palmitoyl-lysophosphatidic acid, or stearoyl-lysophosphatidic acid, or oleoyl-lysophosphatidic acid, or combinations thereof in said phospholipid fractions with the presence of said ovarian carcinoma in said subject.

5. The method of claim 1 wherein the blood specimen is from a patient who has not been diagnosed as having Surgical Stage III or Surgical Stage IV ovarian carcinoma.

6. A method for detecting ovarian carcinoma in a subject comprising the following steps:
    (a) providing a plasma sample substantially free of platelets from the subject;
    (b) preparing a lipid extract from said plasma sample; and
    (c) detecting the presence of lysophosphatidic acid in said lipid extract, wherein the presence of lysophosphatidic acid in said plasma sample is indicative of the presence of ovarian carcinoma in the subject.

7. A method of diagnosing ovarian carcinoma in a subject comprising the following steps:
    (a) preparing a plasma sample from a blood specimen collected from the subject:
    (b) assaying for the presence of lysophosphatidic acid at a concentration of 0.1 $\mu$M or greater in said plasma sample; and
    (c) correlating the presence of lysophosphatidic acid at said concentration of 0.1 $\mu$M or greater in said plasma sample with the presence of said ovarian carcinoma.

8. The method of claim 7 wherein the blood specimen is from a patient who has not been diagnosed as having Surgical Stage III or Surgical Stage IV ovarian carcinoma.

* * * * *